(12) United States Patent
Dilmaghanian (10) Patent No.: US 8,328,587 B2
(45) Date of Patent: Dec. 11, 2012

(54) IN-LINE CONNECTOR STACK WITH TESTING CAPABILITY

(75) Inventor: Farshid Dilmaghanian, Foothill Ranch, CA (US)

(73) Assignee: Bal Seal Engineering, Inc., Foothill Ranch, CA (US)

( * ) Notice: Subject to any disclaimer, the term of this patent is extended or adjusted under 35 U.S.C. 154(b) by 0 days.

(21) Appl. No.: 12/763,125

(22) Filed: Apr. 19, 2010

(65) Prior Publication Data
US 2010/0267265 A1 Oct. 21, 2010

Related U.S. Application Data

(60) Provisional application No. 61/171,043, filed on Apr. 20, 2009.

(51) Int. Cl.
*H01R 13/17* (2006.01)
(52) U.S. Cl. ........................................ 439/827
(58) Field of Classification Search ............. 439/271, 439/736, 668, 669, 527; 29/856, 593; 607/37, 607/508, 836
See application file for complete search history.

(56) References Cited

U.S. PATENT DOCUMENTS

| | | | |
|---|---|---|---|
| 4,072,154 A | 2/1978 | Anderson et al. | |
| 4,105,037 A | 8/1978 | Richter et al. | |
| 4,202,592 A | 5/1980 | Rullier et al. | |
| 4,262,673 A | 4/1981 | Kinney et al. | |
| 4,461,194 A | 7/1984 | Moore | |
| 4,934,366 A | 6/1990 | Truex et al. | |
| 5,331,966 A * | 7/1994 | Bennett et al. | 600/508 |
| 5,413,595 A | 5/1995 | Stutz, Jr. | |
| 5,817,984 A | 10/1998 | Taylor et al. | |
| 5,866,851 A | 2/1999 | Taylor et al. | |
| 6,029,089 A | 2/2000 | Hawkins et al. | |
| 6,192,277 B1 | 2/2001 | Lim et al. | |
| 6,428,368 B1 | 8/2002 | Hawkins et al. | |
| 6,498,952 B2 | 12/2002 | Imani et al. | |
| 6,671,554 B2 | 12/2003 | Gibson et al. | |
| 6,878,013 B1 | 4/2005 | Behan | |
| 6,879,857 B2 | 4/2005 | Swanson et al. | |
| 6,887,229 B1 | 5/2005 | Kurth | |

(Continued)

FOREIGN PATENT DOCUMENTS
WO    WO 97/35636 A1    10/1997
(Continued)

OTHER PUBLICATIONS

International Search Report completed and mailed Sep. 30, 2009 from related International Application No. PCT/US2009/040184, filed Apr. 10, 2009 (3 pages).

(Continued)

*Primary Examiner* — Alexander Gilman
(74) *Attorney, Agent, or Firm* — Klein, O'Neill & Singh, LLP (57) ABSTRACT

Connector assemblies for use with implantable medical devices having easy to assemble contacts are disclosed. The connector assemblies are generally formed by coupling a plurality of ring contacts, sealing rings, and spring contact elements together with at least one holding ring to form a connector having a common bore for receiving a medical lead cable. Contact grooves or spring chambers for positioning the spring contact elements are formed in part by assembling multiple components together. A further aspect is a provision for encasing each connector assembly or stack inside a thermoset layer or a thermoplastic layer before over-molding the same to a sealed housing.

21 Claims, 12 Drawing Sheets

U.S. PATENT DOCUMENTS

| | | | |
|---|---|---|---|
| 6,895,276 B2 | 5/2005 | Kast et al. | |
| 7,003,351 B2 | 2/2006 | Tvaska et al. | |
| 7,047,077 B2 | 5/2006 | Hansen et al. | |
| 7,062,329 B2 | 6/2006 | Ostroff | |
| 7,063,563 B1 | 6/2006 | Hsu | |
| 7,070,455 B2 | 7/2006 | Balsells | |
| 7,083,474 B1 | 8/2006 | Fleck et al. | |
| 7,108,549 B2 | 9/2006 | Lyu et al. | |
| 7,164,951 B2 | 1/2007 | Ries et al. | |
| 7,187,974 B2 | 3/2007 | Haeg et al. | |
| 7,195,523 B2 | 3/2007 | Naviaux | |
| 7,241,180 B1 | 7/2007 | Rentas Torres | |
| 7,263,401 B2 | 8/2007 | Scott et al. | |
| 7,299,095 B1 | 11/2007 | Barlow et al. | |
| 7,303,422 B2 | 12/2007 | Hoffer et al. | |
| 7,326,083 B2 | 2/2008 | Mehdizadeh et al. | |
| 7,429,199 B2 | 9/2008 | Burgess | |
| 7,711,428 B2 * | 5/2010 | Janzig et al. | 607/37 |
| 2006/0224208 A1 | 10/2006 | Naviaux | |
| 2007/0202728 A1 * | 8/2007 | Olson et al. | 439/248 |
| 2007/0239247 A1 | 10/2007 | Camps et al. | |
| 2008/0208279 A1 * | 8/2008 | Janzig et al. | 607/37 |
| 2008/0255631 A1 * | 10/2008 | Sjostedt et al. | 607/37 |
| 2009/0048638 A1 * | 2/2009 | Rey et al. | 607/37 |

FOREIGN PATENT DOCUMENTS

| | | |
|---|---|---|
| WO | WO 2004/030753 A1 | 4/2004 |
| WO | WO 2009/126872 A2 | 10/2009 |

OTHER PUBLICATIONS

Written Opinion completed and mailed Sep. 30, 2009 from related International Application No. PCT/US2009/040184, filed Apr. 10, 2009 (3 pages).

Office Action mailed Sep. 2, 2009 from related U.S. Appl. No. 12/421,874, filed Apr. 10, 2009.

Office Action mailed Dec. 15, 2009 from related U.S. Appl. No. 12/421,874, filed Apr. 10, 2009.

Office Action mailed Feb. 26, 2010 from related U.S. Appl. No. 12/421,874, filed Apr. 10, 2009.

Extended European Search Report dated Aug. 11, 2010 from corresponding European Application No. 10 004 189.6 (9 pages).

* cited by examiner

IN-LINE CONNECTOR STACK WITH TESTING CAPABILITY

CROSS-REFERENCE TO RELATED APPLICATIONS

This is a regular U.S. application of provisional application No. 61/171,043, filed, Apr. 20, 2009, which incorporates by reference the description of application Ser. No. 12/421,874, filed Apr. 10, 2009, which is a regular utility application of Ser. No. 61/044,408, filed Apr. 11, 2008. The contents of the foregoing applications are expressly incorporated herein by reference for all purposes.

BACKGROUND

Implantable medical devices for providing electrical stimulation to body tissues, for monitoring physiologic conditions, and for providing alternative treatments to drugs are well known in the art. Exemplary implantable medical devices include implantable cardio defibrillators, pacemakers, and programmable neurostimulator pulse generators, which are collectively herein referred to as "implantable medical devices" or IMDs. These IMDs typically incorporate a hermetically sealed device enclosing a power source and electronic circuitry. Connected to the sealed housing, also known as a "can," is a header assembly. The header assembly includes electrical contact elements that are electrically coupled to the electronic circuits or to the power source located inside the can via conductive terminals. The header assembly provides a means for electrically communicating, via an external medical lead cable, the electronic circuits or power source located inside the device with the actual stimulation point.

Industry wide standards have been adopted for, among other things, the dimensions, size, pin spacing, diameter, etc. for the receptacle and the medical lead cable. Furthermore, good electrical contact must be maintained during the life of the implantable medical device and the medical lead cable for use with the IMD must not disconnect from the receptacle located in the header, yet be detachable for implanting and programming purposes and for replacing the IMD when necessary.

Although prior art connector contacts provide viable options for medical device manufacturers, the IMD discussed herein and the various headers provide many benefits to manufacturers and practitioners. Furthermore, in-line connectors, while discussed with specific implantable applications, may be used in other industries and applications, including consumer electronics, electrical connectors, and industrial electronics, such as aviation, automotive, oil and gas, etc.

SUMMARY

Broadly speaking, in-line connector stacks are disclosed. Examples include in-line connector stacks placed inside an encapsulation layer so that the encapsulated stack may be tested for aligning and conductivity before it is installed or placed into a header of an IMD. Different in-line connector stacks comprising different seal and conductive elements may be used with the encapsulation layer concept of the present application. Furthermore, while the specification describes specific applications of the connector stacks in combination with a header of an IMD, the stacks may be used in other applications and industries requiring multiple conductive sources in an in-line configuration.

An exemplary method is directed to a method for manufacturing an in-line connector. In one specific example, the method comprising encapsulating an in-line connector stack comprising a common bore with an encapsulation layer to form an encapsulated stack comprising two end surfaces; wherein a plurality of seal elements and conductive contact elements are located between the two end surfaces; aligning a plurality of slots formed on the encapsulation layer with the plurality of conductive contact elements; placing two end caps at the two end surfaces of the encapsulation layer to retain the plurality of seal elements and conductive contact elements inside the encapsulation layer; and wherein the encapsulated stack comprises a common bore and two end openings.

An exemplary apparatus comprises a header assembly comprising a header comprising a bore, an in-line connector stack comprising a plurality alternating seal elements and conductive contact elements encapsulated by an encapsulation layer positioned inside the bore, and a snap fit end cap comprising a bore mechanically engaged to the header, which defines a seam therebetween, and wherein the header comprises a plurality of slots aligned with a plurality of slots formed on the encapsulation layer.

A further exemplary method is directed to a method for manufacturing an in-line connector. The method, for example, may comprise the steps of forming an encapsulated stack by placing a plurality of seal elements, springs, and conductive contact elements through an opening of a cylindrical housing comprising a bore and a plurality of slots formed laterally of the opening; engaging an end cap to the opening of the cylindrical housing; aligning the plurality of slots on the cylindrical housing with the plurality of conductive contact elements; and testing the encapsulated stack by applying an electrical signal across one of the conductive contact elements.

BRIEF DESCRIPTION OF THE DRAWINGS

The following drawings form part of the present specification and are included to further demonstrate certain aspects of the disclosed IMDs, connector stacks, and headers. The present embodiments may be better understood by one or more of these drawings in combination with the detailed description of examples presented herein.

DETAILED DESCRIPTION

The detailed description set forth below in connection with the appended drawings is intended as a description of the presently preferred embodiments of apparatus, system and method for making and using IMDs, in-line connector stacks, and headers and is not intended to represent the only forms in which they may be constructed or utilized. The description sets forth the features and the steps for constructing and using the IMDs, in-line connector stacks, and headers of the present examples in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like or similar elements or features.

Figures 1A, 2A, 3A:
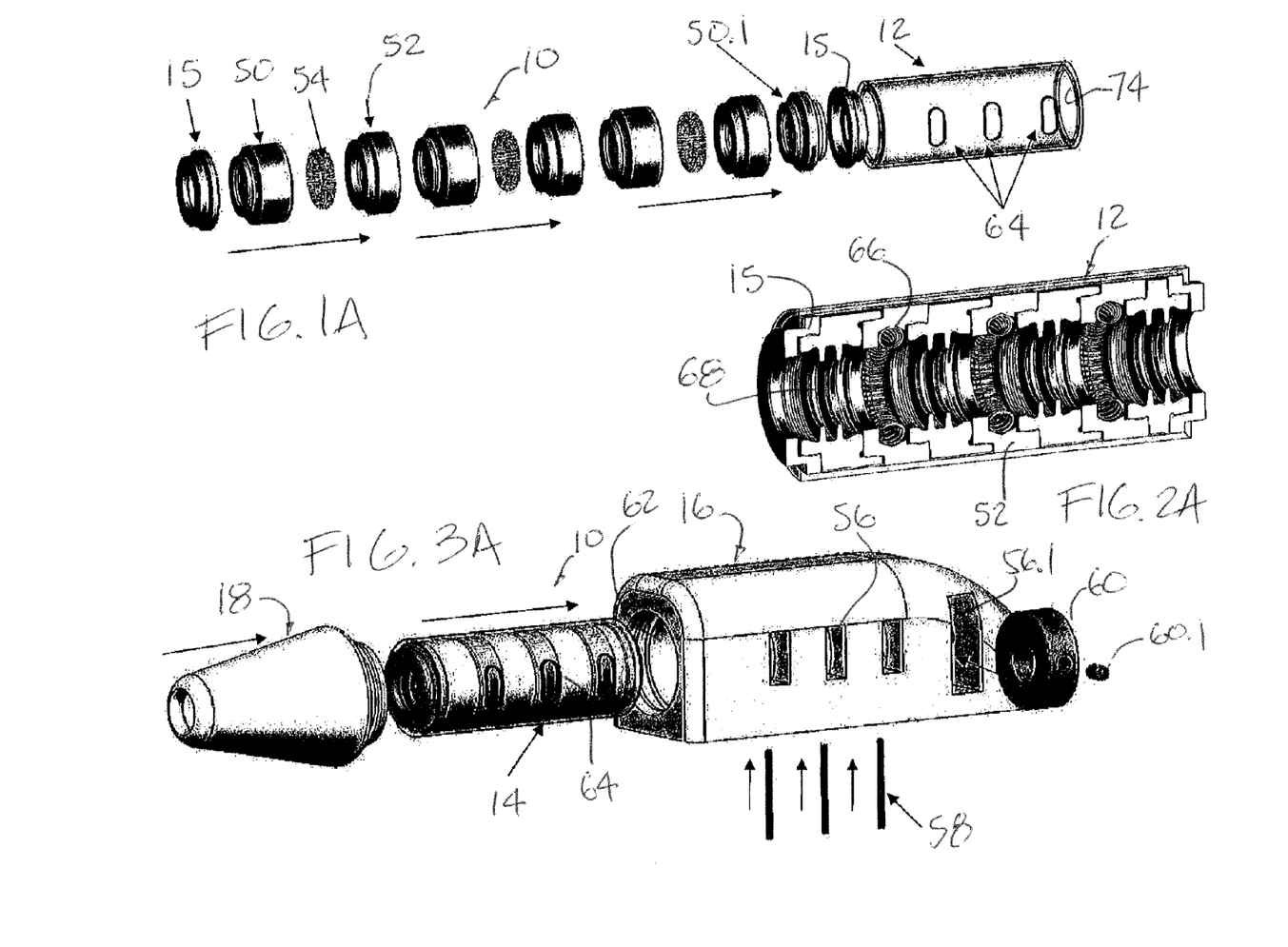
FIGS. 1A, 2A, 3A, 4A, 5A, 6A, and 7A show an in-line connector stack of alternating conductive and non-conductive elements, an encapsulation layer for receiving the in-line connector stack, a header for receiving the encapsulated stack, and a sealed electronic case for mating with the header.
Figure 1D:
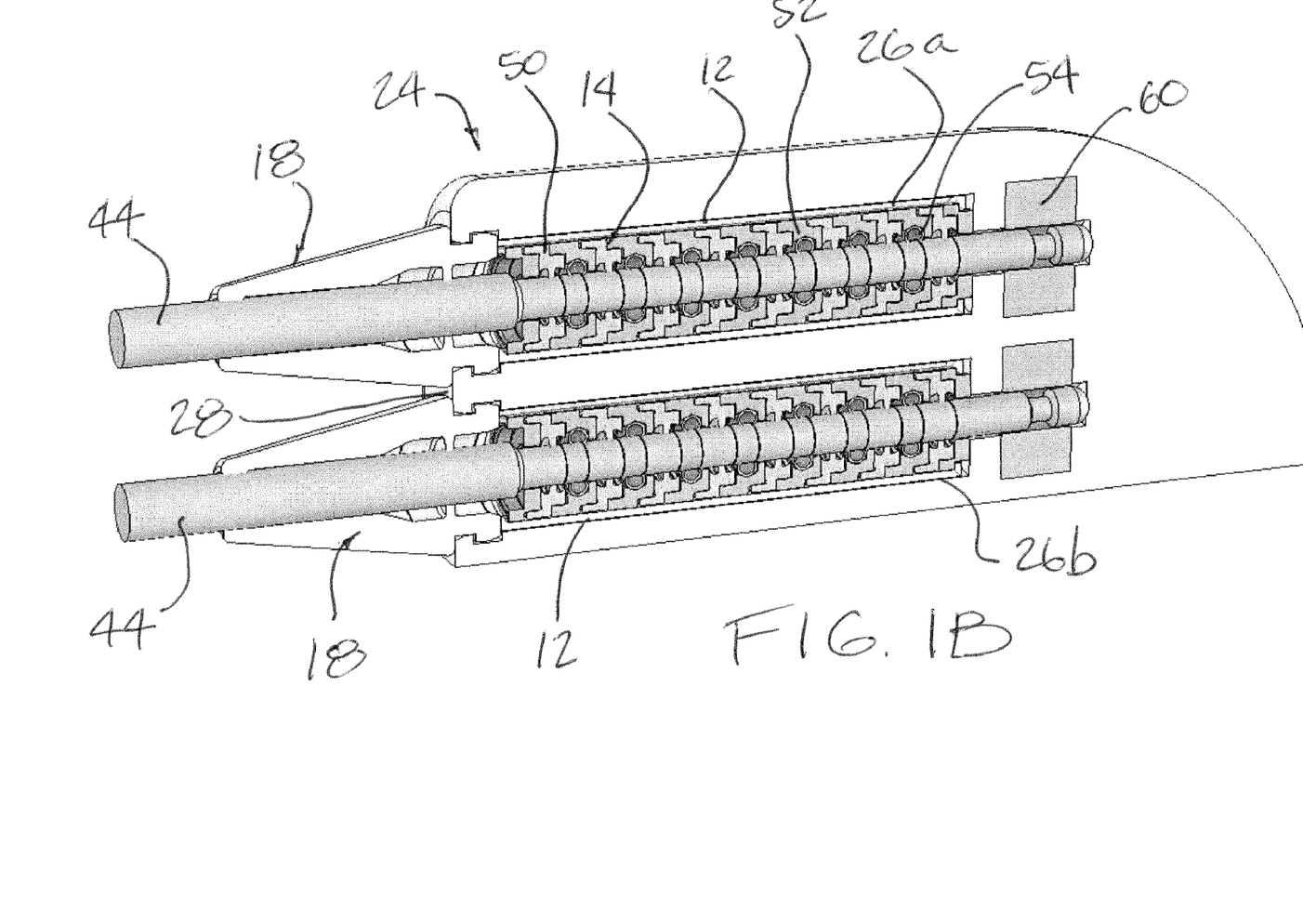
FIGS. 1B, 2B, and 3B show a header comprising two in-line connector stacks, which are positioned in respective encapsulation layers.

FIG. 1A to FIG. 7A show a stackable connector in various stages of assembly and different views for clarity. The connector stack 10, which comprises a plurality of seal elements 50, conductive elements 52, and spring contact elements 54, are configured to fit inside an encapsulation layer 12 to form an encapsulated stack 14. The encapsulated stack 14 is configured to fit inside a molded header 16, which has slots 56 or openings for accessing to weld the leads 58 from the electronic case (See, e.g., FIGS. 7A and 5B) with the conductive elements 54. The openings 56 are then back filled with a curable implantable material, such as silicone and other medical grade elastomers or resins. Another opening 56.1 may be provided for inserting a holding ring 60 with a locking screw 60.1 for more permanently securing the lead cable 44 to the connector stack, as shown in FIG. 6A. In one embodiment, end caps 15 are incorporated, either at only one end of the stack 10 or at both ends, as shown in FIG. 1A in exploded view. The end caps 15 are positioned adjacent an end seal element 50.1 and provide engagement with the encapsulation layer 12. In one example, the end caps 15 provide added sealing by incorporating interior ribs or rings for sealing against the electrical lead cable 44. The end caps 15 may have the same or higher durometer as the seal element but may be lower to facilitate insertion at the inlet. The end seal element 50.1 may be similar to the middle seal elements but also includes sealing means, such as ribs and projections, for sealing against the end cap.

As shown, the encapsulation layer 12 comprises a generally cylindrical tube comprising one or more slots 64. In one example, the number of slots 64 corresponds to the number of conductive contact elements 52, which can vary depending on the desired applications and electrical contacts. The encapsulation layer 12 comprises a lip 74 at each end for engaging the end cap 15. As shown, the in-line stack 10 comprises three conductive elements. However, less than or more than three may be incorporated without deviating from the spirit and scope of the present invention. When installed into the header 16, the slots 64 on the insulation layer 12 align with the slots 56 on the header 16 so that leads 58 from the can 22 may be accessed and attached to the conductive elements 52.

Figures 4A, 5A, 6A, 7A:
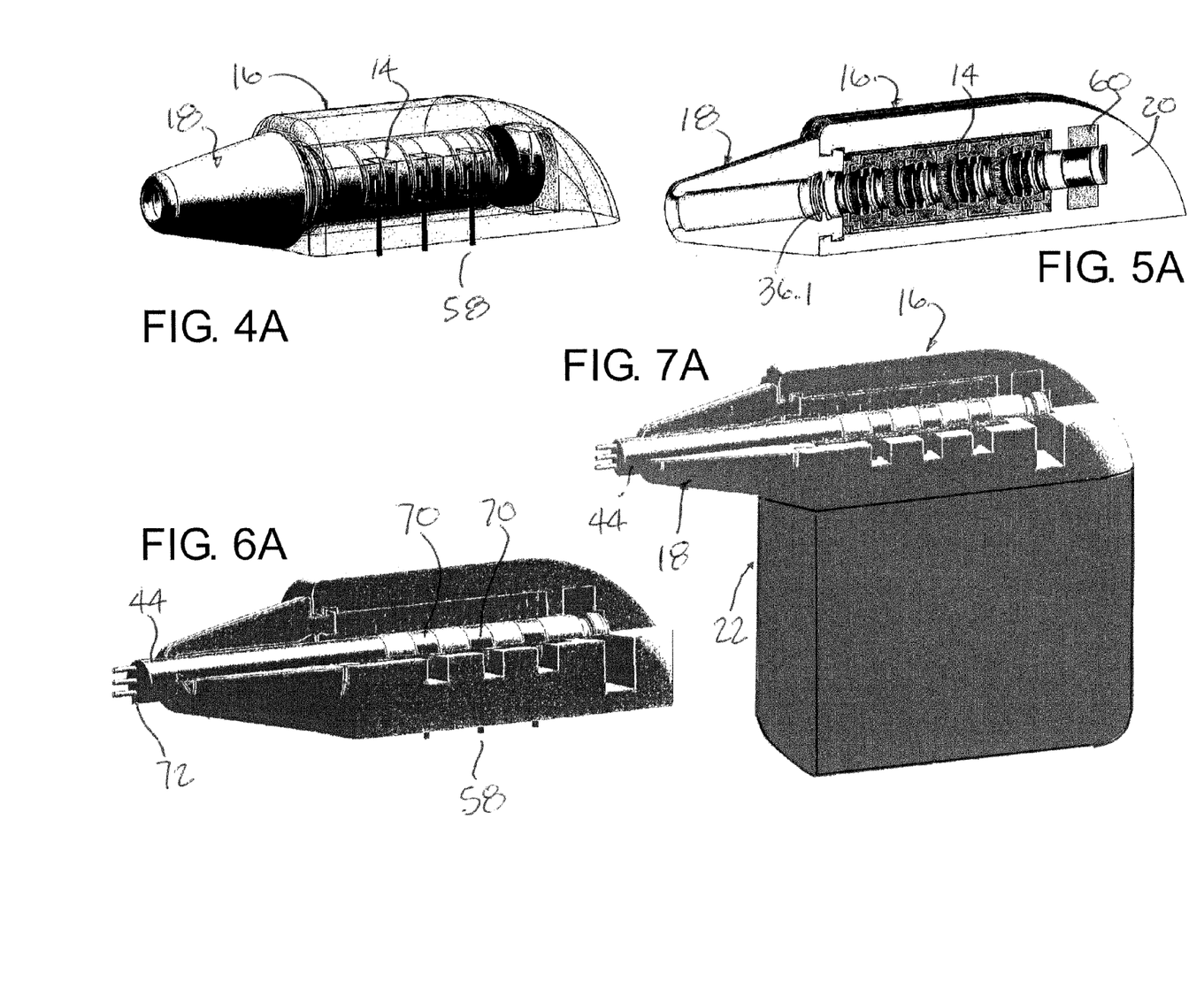

Thus, a feature of the present assembly, method and device for making and using an IMD, in-line stack, and header is understood to include a plurality of alternating seal elements 50 and conductive elements 52 located inside an encapsulation layer 12 comprising a plurality of slots 64, and wherein the plurality of slots align with a corresponding number of conductive elements 52. In one specific example, a canted coil spring 54 is in electrical contact with each conductive element 52. As shown in FIG. 2A, the canted coil spring 54 is located within a groove 66 formed along the inside bore 68 of the in-line stack, which is common with the bore 62 of the header 16. In a particular embodiment, the groove 66 is formed utilizing a back wall and a side wall of a conductive contact element 52 along with a side wall of an adjacent seal element 50. However, the groove 66 may be formed using different features and walls utilizing different conductive rings and seals than as shown, such as that shown in FIG. 11, further discussed below. Signals or current passing from the leads 58 (FIG. 3A) of an electrical housing or case are configured to pass through corresponding conductive elements 52 which then pass through corresponding springs 54 and to corresponding electrode ring terminals 70 on the lead cable 44, which then pass through corresponding electrode leads 72 (FIG. 6A).

In one embodiment, a snap fit end cap 18 is incorporated for securing the encapsulated stack 14 inside the header bore 62 of the header 16, as shown in FIGS. 3A-5A. The snap fit end cap 18 has provisions for engaging the header 16 and for providing an axial force on the encapsulated stack 14 to at least slightly compress the stack inside the header. For example, the snap fit end cap 18 and the header 16 may incorporate interference detent arrangements that snap in place utilizing axial interference. A seam is defined between the end cap 18 and the header 16, which is sealed by the force or pressure of the snap fit arrangement. In another example, curable implantable material is applied to further seal the seam. As shown, one or more raised bumps or ribs 36.1 are incorporated in the bore of the end cap 18 for sealing against the exterior surface of a lead cable. The one or more raised bumps or ribs 36.1 would provide additional sealing from potential leakage into the bore of the in-line stack in addition the seal elements.

By stacking the connector stack 10 into an encapsulation layer 12 and encapsulating it as a stack unit 14, the stack is aligned and can optionally be tested before placing the stack 14 into the header. In other words, the encapsulated stack unit 14 may be viewed a free-standing axially compressed stack that is aligned and adapted to receive an electrical lead cable 44 (FIGS. 6A and 7A). Thus, a technician can better perform quality control on the stack 14 before placing it into a header 16 or into a connector housing and then molding it in place with resin. Previously, a technician can only test the stack after it has been assembled onto the electrical case 22 (FIG. 7A), which can only be done by installing the same into a header 16. For example, a technician can test the stack unit 14 as shown in FIG. 2A by inserting a lead cable into the stack bore 68 and applying signals or current through the slots 64 to electrically communicate with the aligned conductive elements 52. As such, the in-line connector stack 14 has utility independent of being placed into the header 16 and/or for use with an implantable device.

Refer again to FIG. 1A, the encapsulation layer 12 may be made from thermoplastic or TPE material and preferably non-conductive. In one example, the encapsulation layer is made from a thermoset plastic and comprises a generally cylindrical shape structure comprising slots 64 and end lips 74 for retaining or engaging the end caps 15. In an alternative embodiment, one or two end seals 50.1, which are seal elements located at the two ends of the stack 10, are configured to seal against the lead cable and also function to engage the encapsulation layer 12. In this alternative embodiment, end caps 15 may be eliminated.

In an alternative embodiment, a locking ring with a locking screw is incorporated in the snap fit end cap 18 (FIG. 4B) for securing the lead cable.

In an alternative embodiment, the end cap 18 is integrally formed with the header 16 and a rear opening (not shown) is instead incorporated on the header, near element 20 of FIG. 5A. In this alternative embodiment, the stack unit 14 would be installed through the rear opening, which is subsequently back filled with a curable resin.

In an alternative embodiment, the connector stack 10 is made from particular seal elements and ring contact elements as described in the '874 application. In still other embodiments, the connector stack is made from particular seal elements and ring contact elements as described in provisional application Ser. No. 61/240,157, filed Sep. 4, 2009, the contents of which are expressly incorporated herein by reference. In still yet other embodiments, the connector stack 10 is made from particular seal elements and ring contact elements as described in co-pending application Ser. No. 12/062,895, filed Aug. 4, 2008, the contents of which are expressly incorporated herein by reference.

In an alternative embodiment, the encapsulated stack 14 is over molded with a polymeric header casting resin instead of being inserted into the pre-formed header 16 as shown. The over molded header in this alternative embodiment, not including the pre-formed header 16, is then attached to an electronic case, i.e., sealed can, of an implantable medical device 22.

FIGS. 1B to 3B show yet another alternative header assembly 24 comprising a double bore arrangement 26a, 26b. Each bore is configured to store an encapsulated stack 14, similar to the embodiment of FIGS. 1A to 7A, and has a snap fit end cap 18 for retaining the stack 14 inside the bore. In one embodiment, a center rib 28 incorporates two detents in superjacent format. The two detents in superjacent format are configured for snap fit engagement with the end caps 18.

Figure 2B:
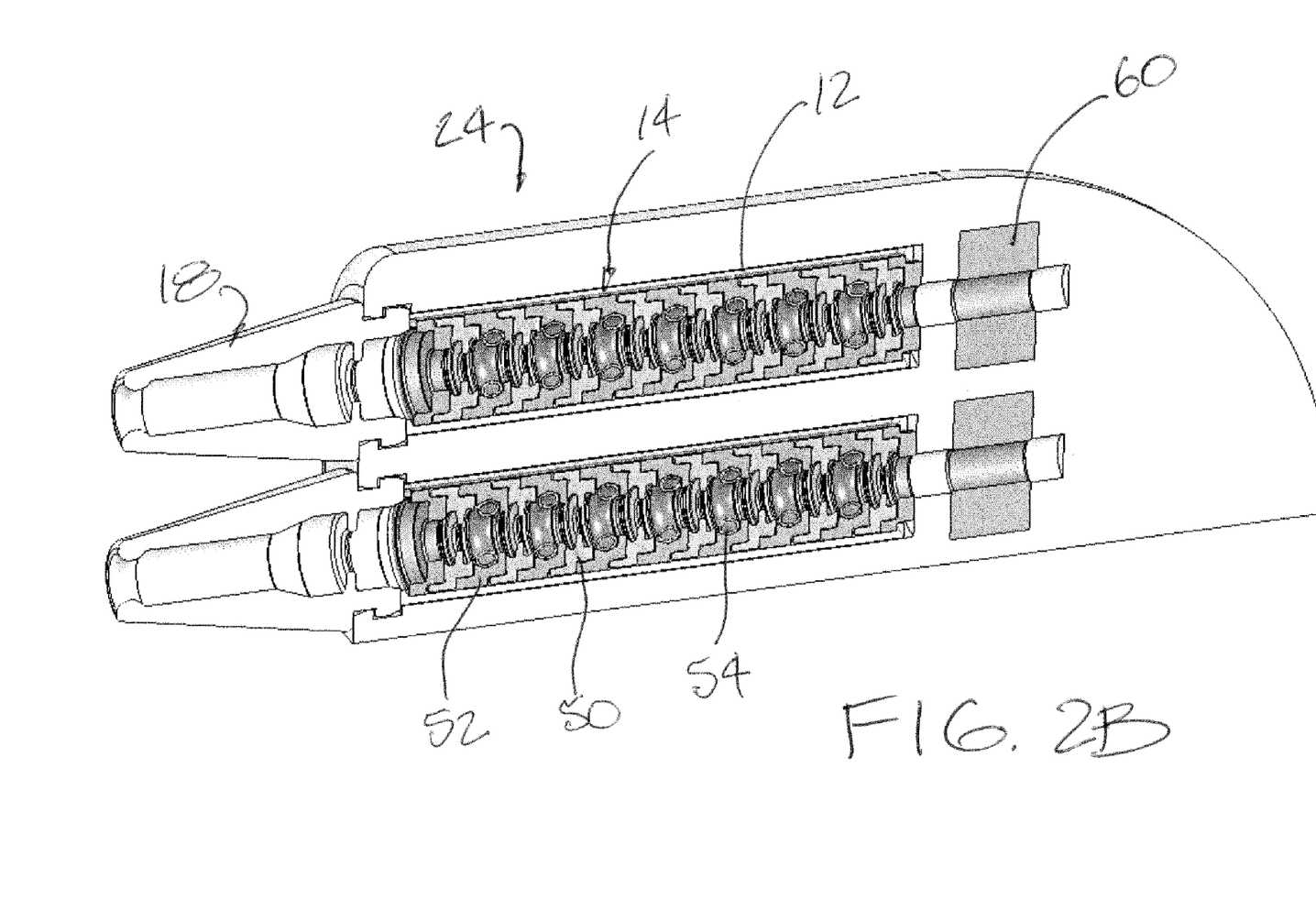
Figure 3B:
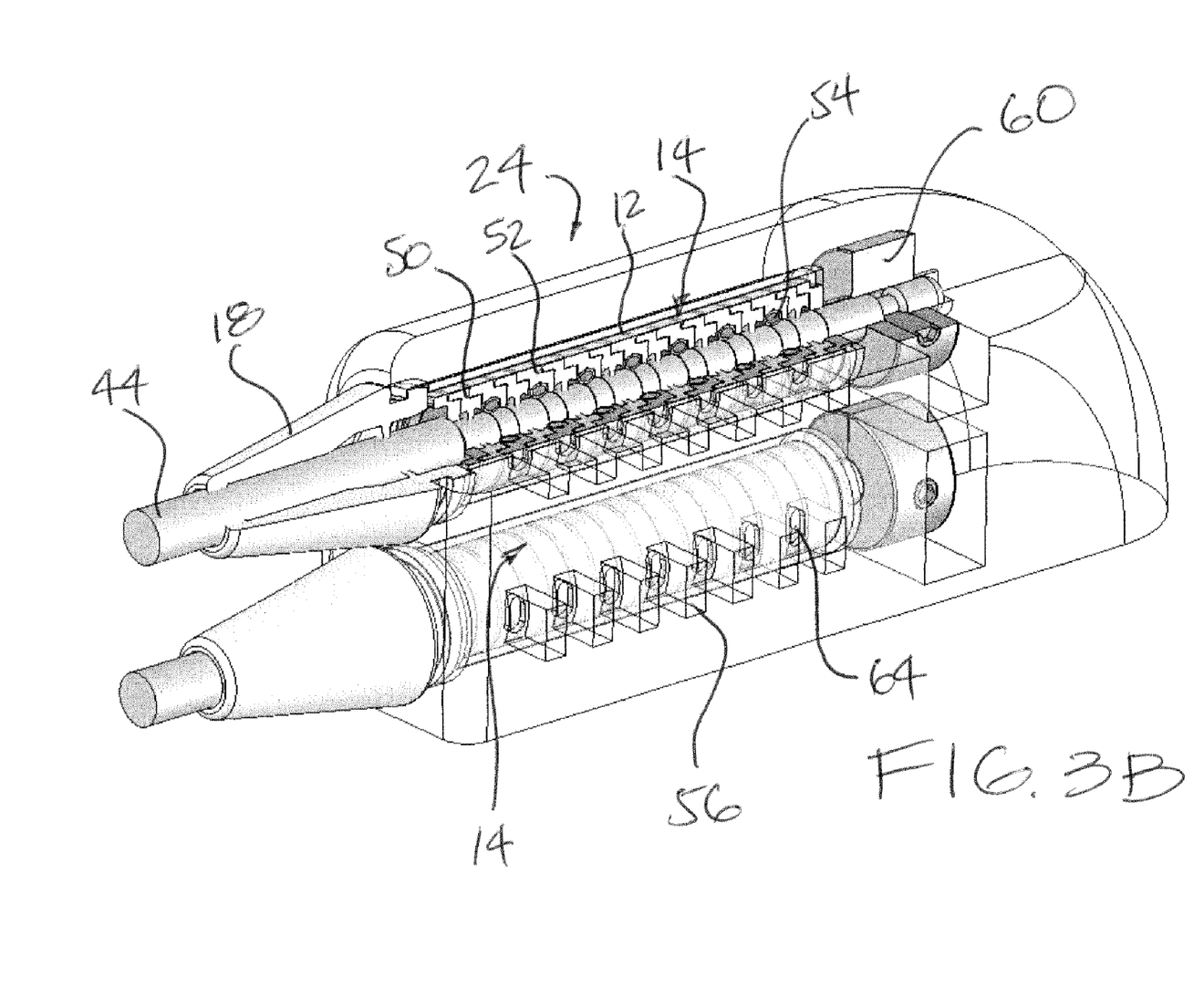

In an alternative embodiment, the header 24 is configured to receive the two connector stacks 14 in a side-by-side configuration instead of one on top of another as shown in FIG. 2B. In other embodiments, more than two connector stacks 14 may be incorporated into the header 24 in a side-by-side configuration, one on top of another configuration, or a pyramid type configuration.

Referring now to FIGS. 4B to 6B, a set screw block 30 having a set screw 32 is incorporated in the snap fit end cap 34. An opening 34.3 is thus provided on a side of the frustoconical cone section of the end cap 34 to provide access to the set screw 32. The opening 34.3 may be back-filled with an implantable material or resin after the set screw 32 is turned to tighten against the lead cable 44 (FIG. 5B). The sect screw block 30 may be made from a plastic material and co-molded with the snap fit end cap 34. In one embodiment, seal elements 36 having annular seal ribs are co-molded or over-molded with the end cap 34 for sealing against a lead cable. The seal elements 36 may be made from the same material as the seal elements 50, which may be an elastomer or a thermoplastic elastomer (TPE), and inserted into the end cap 34.

In an alternative embodiment, the end cap 34 is integrally molded with the header 24 and the header is provided with a rear opening, near element 20 (FIG. 5B). The encapsulated stack 14 may be placed into the bore of the header through the rear opening. The opening may then be back filled with an implantable material. A snap fit cap or flange (not shown) may also be used to close the rear opening instead of simply back filling the rear opening with a resin. The snap fit cap or flange may be use by itself to seal the rear opening or in combination with curable resin.

Figure 4B:
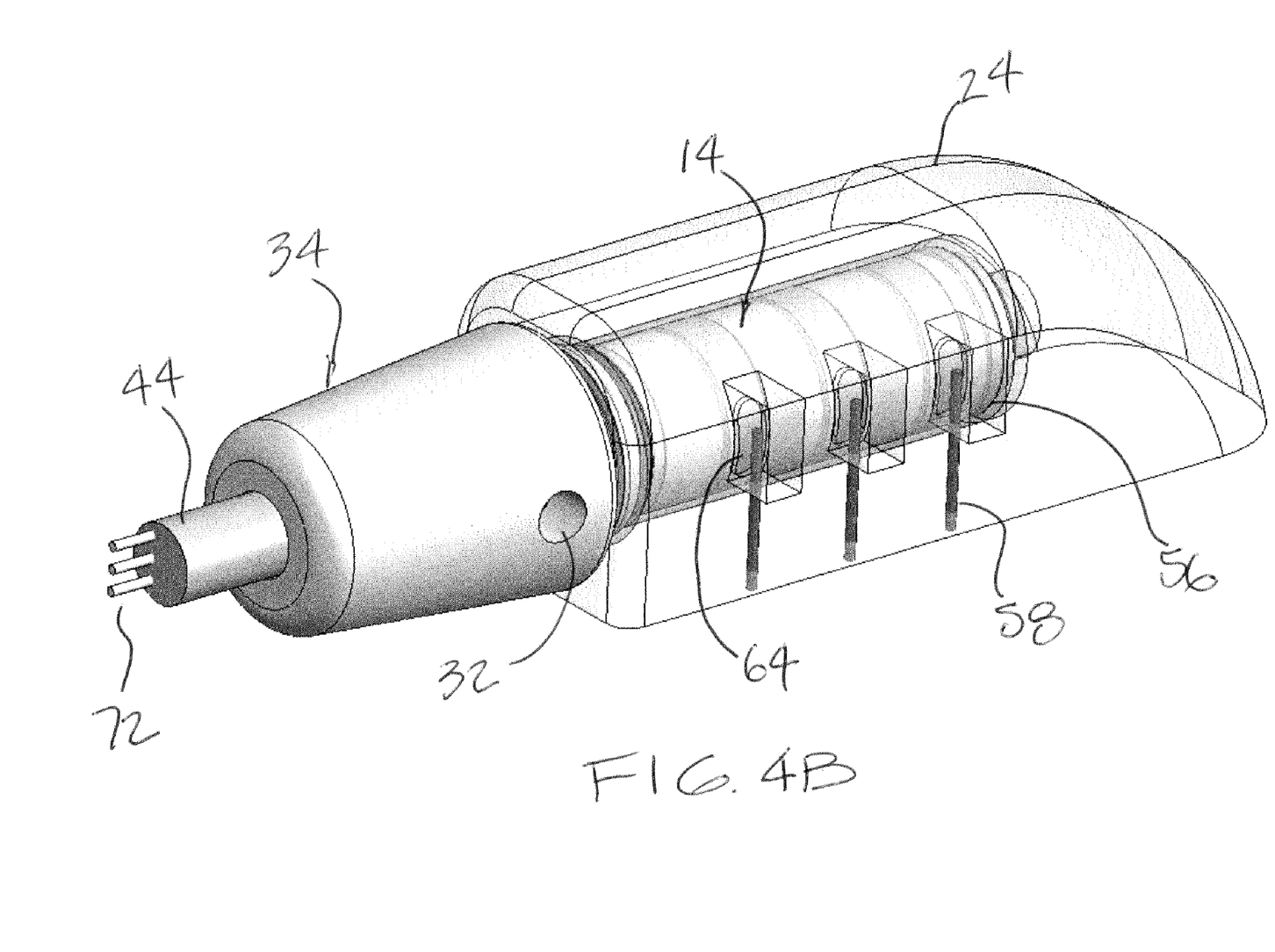
FIGS. 4B, 5B, and 6B show a header attached to an electronic case comprising an encapsulated in-line stack and an integrated snap fit end cap comprising a holding ring.
Figure 5D:
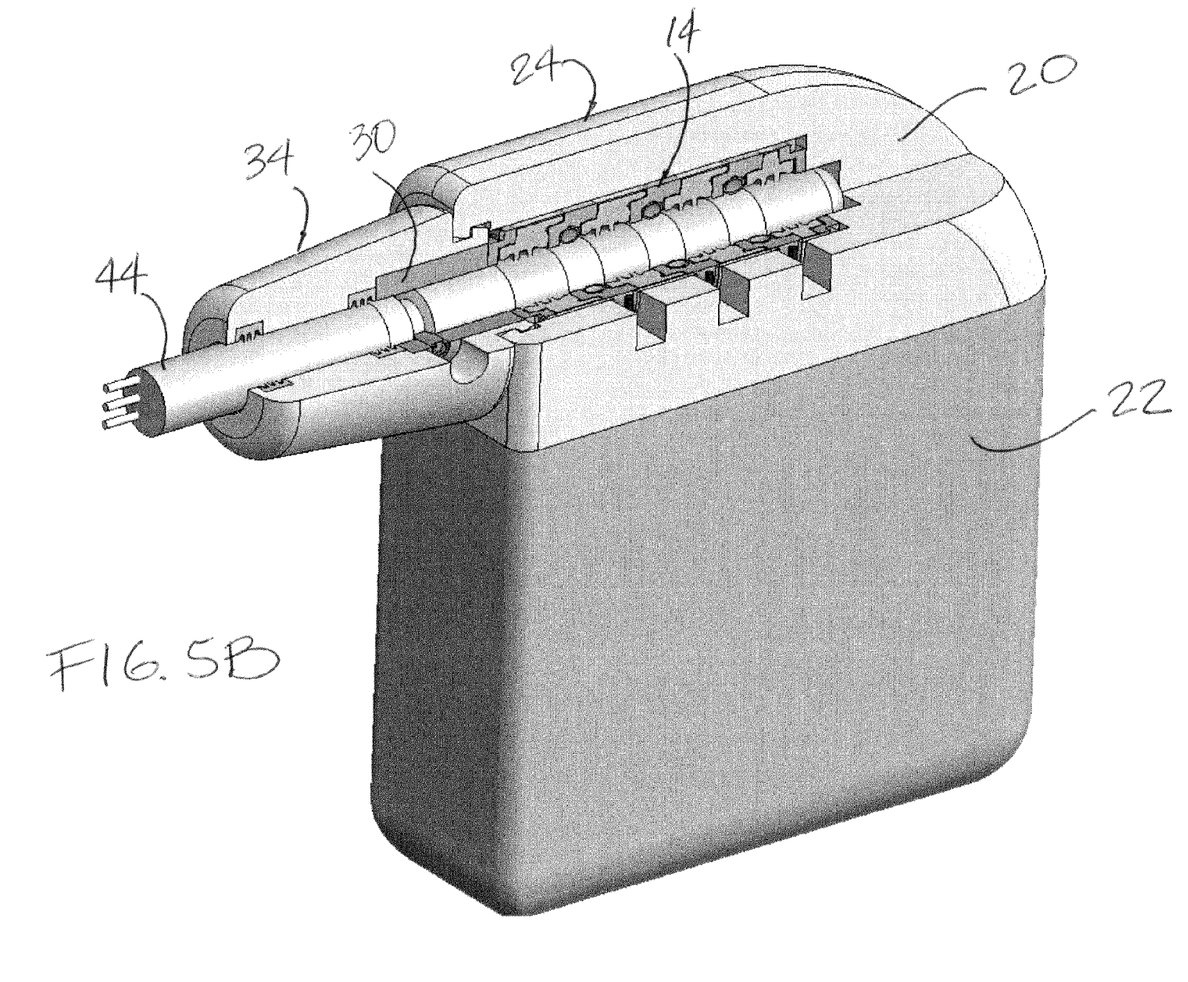

Also shown in the perspective transparent view FIG. 4B are three windows or slots 56 for accessing the leads 58 from the electrical case (not shown), such as a sealed can of an IMD. The windows are understood to be backfilled with an implantable material or resin after the leads are secured to the conductive ring contact elements.

Also shown in the perspective view of FIG. 4B is a set screw opening on the snap fit end cap 34. As such, an opening on the header for a separate holding ring with set screw may be eliminated.

Also shown in the cut-away perspective view of FIG. 5B is an assembled implantable medical device 22 with a lead cable 44 inserted into the common bore of the encapsulated stack 14. The implantable medical device 80 may be any number of devices, such as an implantable cardio defibrillator, pacemaker, and programmable neuro-stimulator pulse generator, to name a few.

Figure 6B:
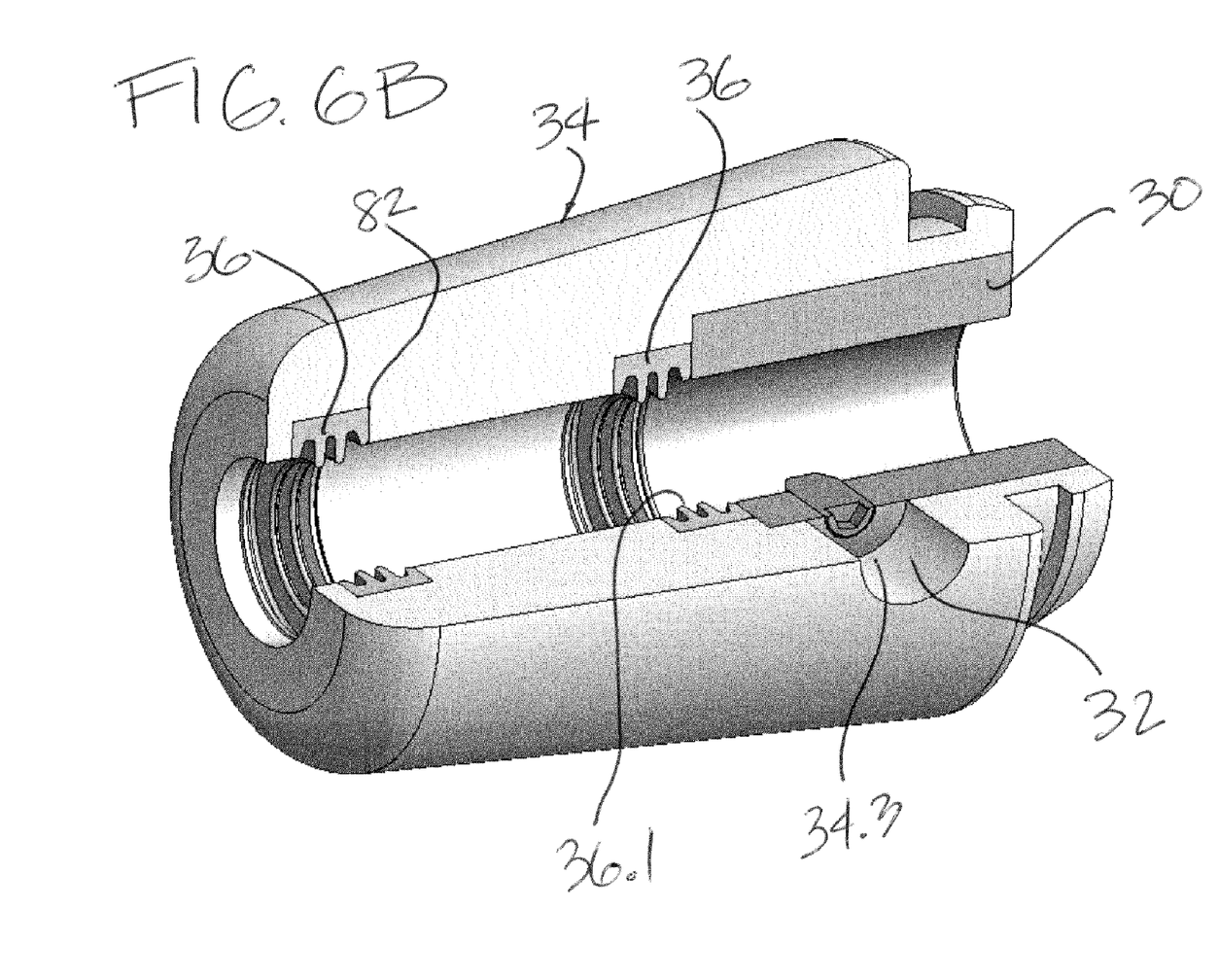

Also shown in the cut-away perspective view of FIG. 6B are a set screw block 30 and two seal inserts 36. In one example, the snap fit end cap 34 is made from a plastic material and is molded with at least one groove 82 for receiving the relatively softer sealing ring 36 comprising raised bumps or ribs 36.1, such as made from silicone or a TPE material, which is separately formed and installed into the groove 82. In another embodiment, the components are co-molded.

Figure 8:
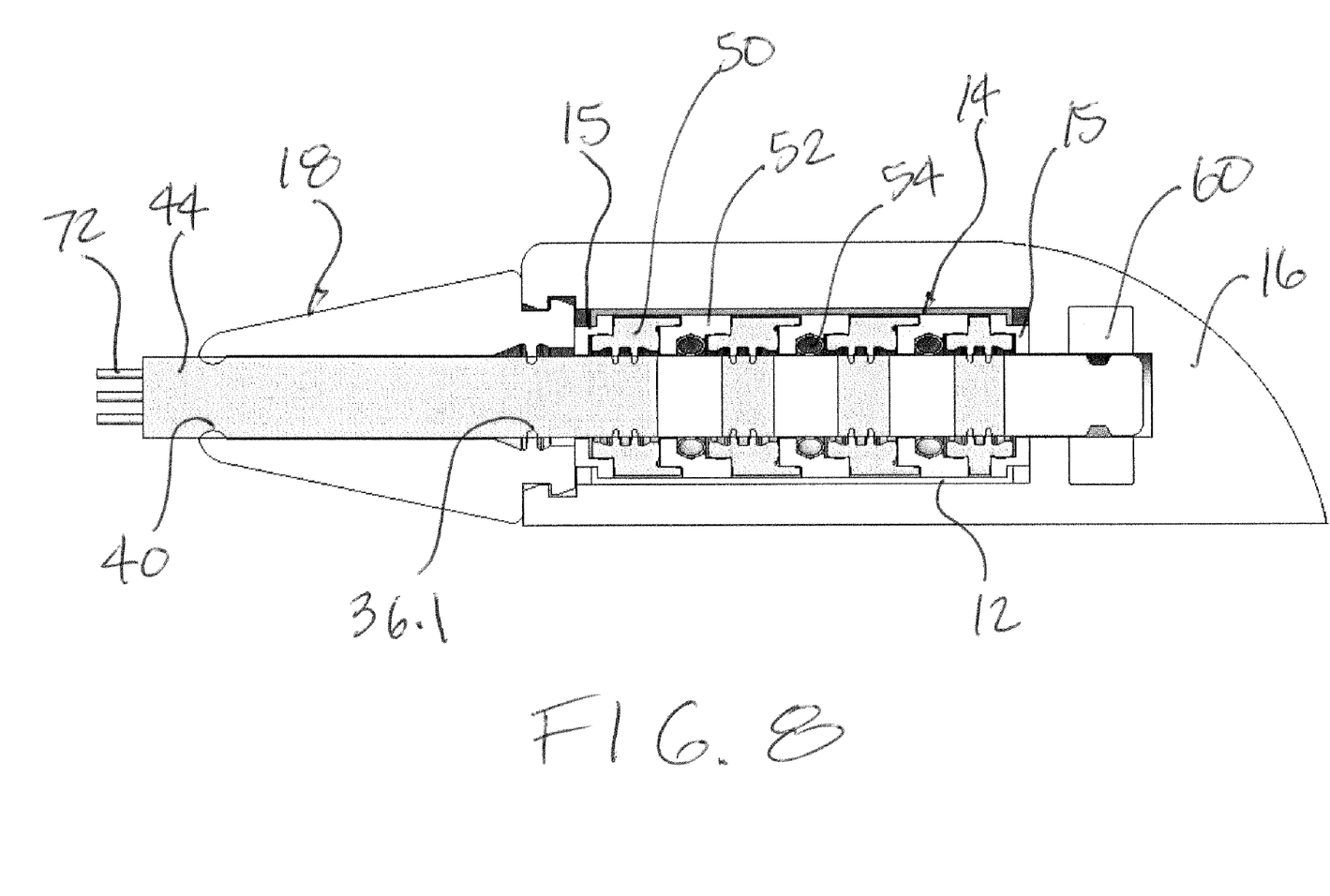
FIG. 8 is a cross-sectional side view of the header of FIG. 4A.

FIG. 8 is an enlarged cross-sectional side view of an exemplary header assembly, which is similar to that shown in FIGS. 1A and 2B. The snap fit end cap 18 is provided with an annular lip seal 40 near the mating end and near the inlet or entrance to the bore of the end cap.

Figure 9:
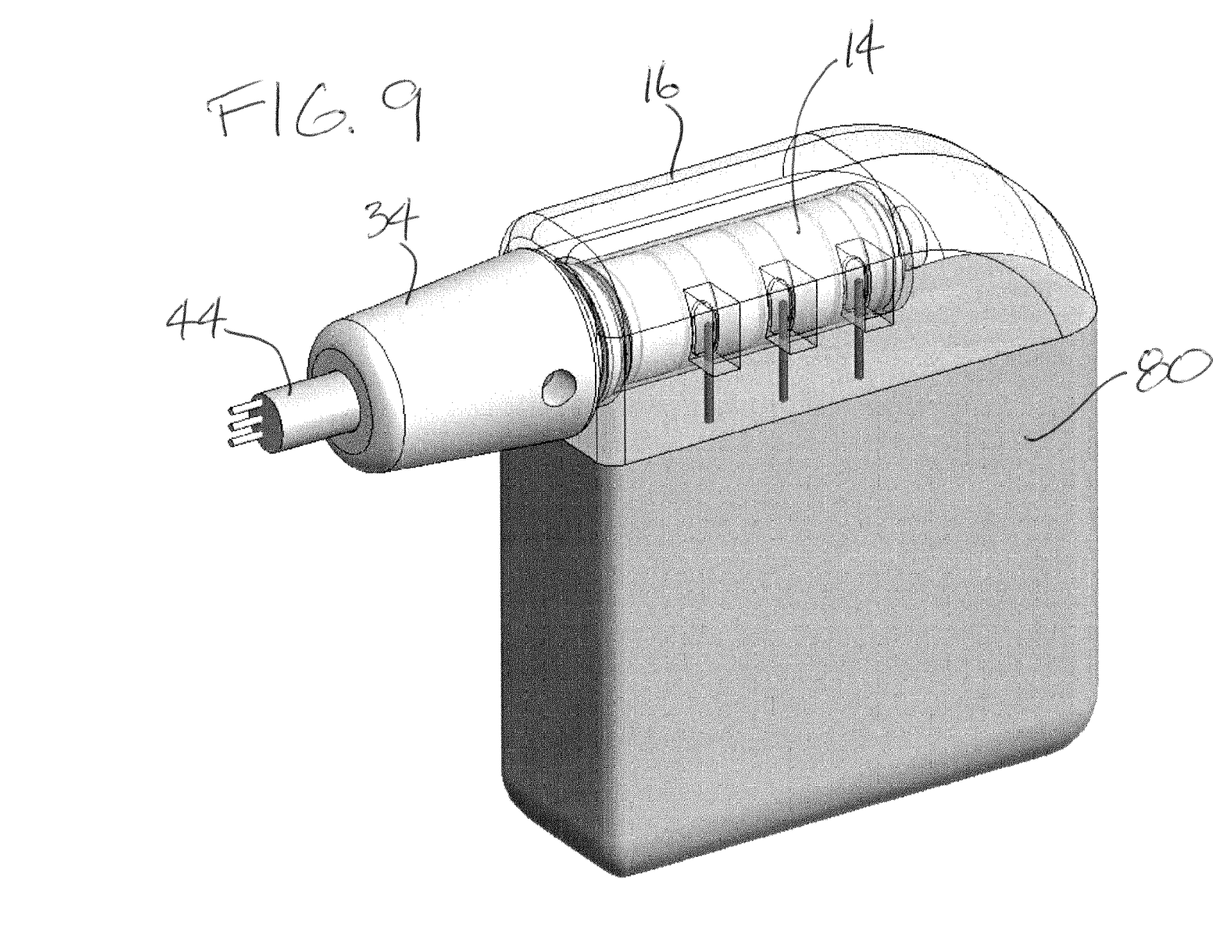
FIG. 9 is a semi-schematic perspective view of the header of FIG. 4B attached to a sealed electronic housing.

FIG. 9 is a perspective semi-transparent view of the assembly of FIG. 4B attached to an electronic case 80.

Figure 10:
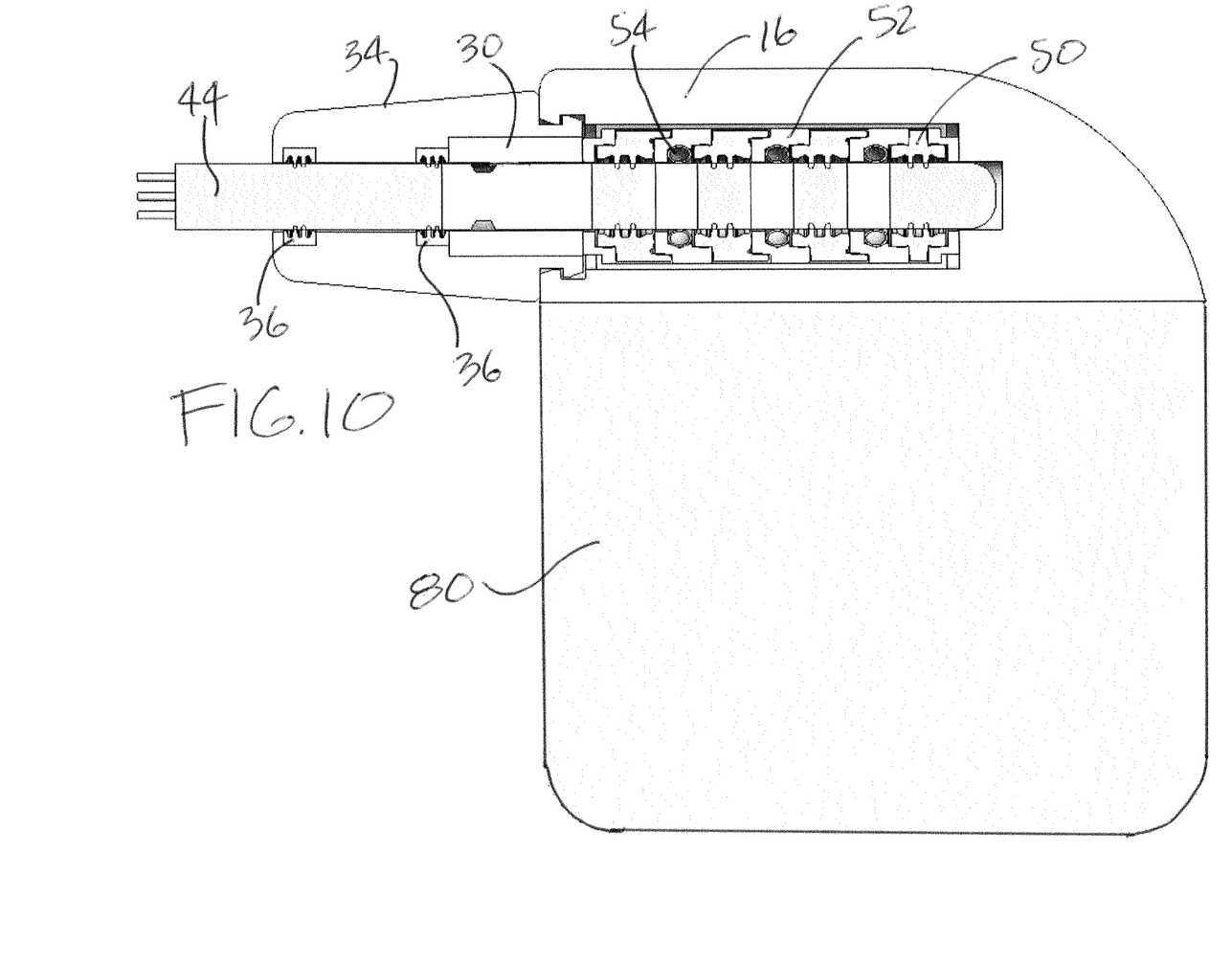
FIG. 10 is a semi-schematic partial cross-sectional side view of the device of FIG. 9.

FIG. 10 is a cross-sectional side view of the assembly of FIG. 9.

Figure 11:
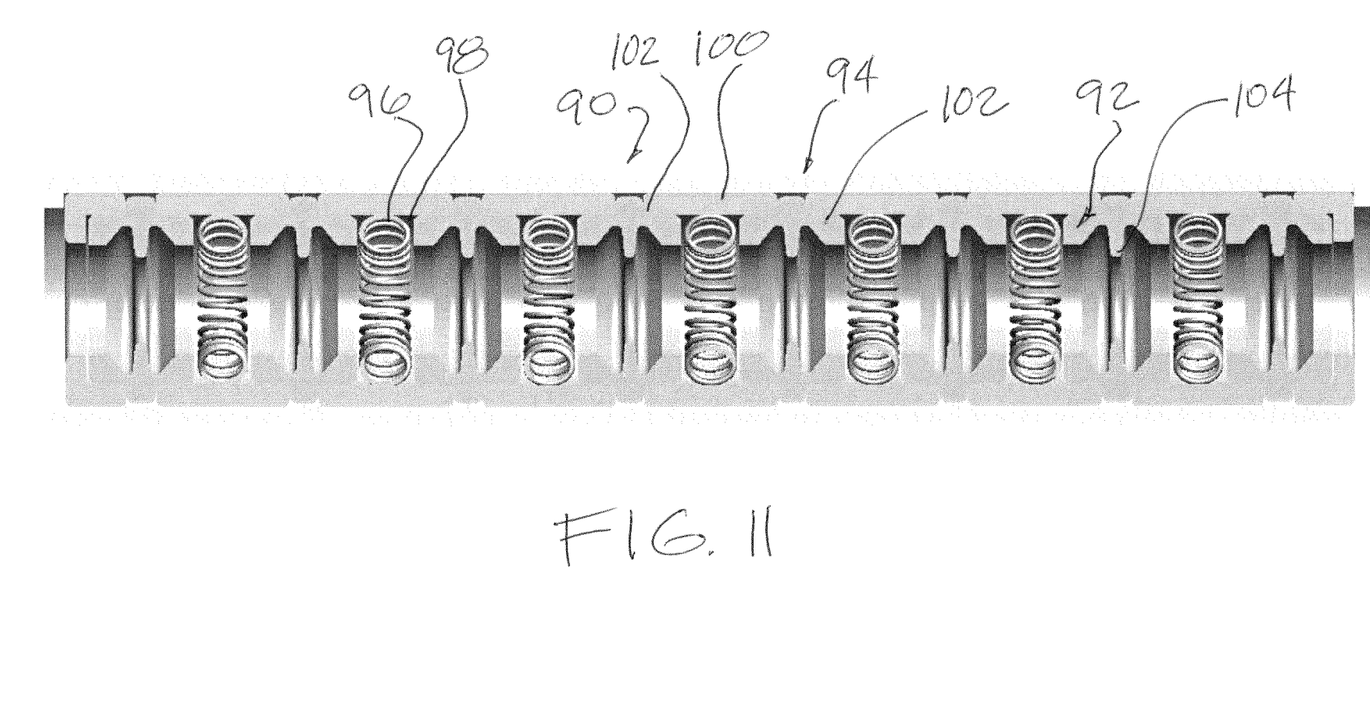
FIG. 11 is a semi-schematic cross-sectional side view of an alternative encapsulated stack.

FIG. 11 is a cross-sectional side view of an encapsulated stack 90 provided in accordance with alternative embodiments, which comprises an in-line stack 92 positioned inside an encapsulation layer 94. Also shown are conductive energizers 96, which separately sit in grooves 98 formed by a conductive element 100 and two adjacent seal elements 102. Note that the conductive elements 100 do not include side walls. As such, the grooves 98 are each formed by a conductive element 100 and two adjacent seal elements 102. The seal elements are each shown with a single projection or lip 104 for sealing against a lead cable. In other embodiments, two or more lips 104 may be incorporated. In the various examples disclosed herein, an encapsulated stack comprising an in-line stack positioned in side an encapsulation layer is provided, which have slots or openings formed on the side thereof for aligning with respective conductive elements. The encapsulated stack, which may be sized to fit any number of contacts as required for a particular application, is configured to facilitate assembly and testing before the encapsulated stack is completed inside a header, connector, or other in-line assembly.

Although limited preferred embodiments and methods for making and using connector assemblies provided in accordance with aspects of the present invention have been specifically described and illustrated, many modifications and variations will be apparent to those skilled in the art. For example, various material changes may be used, incorporating different mechanical engagement means to attach the various components to one another, making use of two or more different materials or composites, making a sealing ring from multiple pieces rather than a singularly molded piece, etc. Still alternatively, the connector assembly may be used for any device that requires an in-line connection in which multiple conductive sources are to be relayed between a source generator and a source receiver, whether that device is configured for implanting or otherwise. Still furthermore, although thermoset and thermoplastic polymers are described for encapsulating a stack, other means may be used, such as a mechanical clamp. Also, aspects and features discussed for one embodiment may be used with other embodiments provided the combined embodiment is compatible. Accordingly, it is to be understood that the connector assemblies constructed according to principles of this invention may be embodied in other than as specifically described herein. The invention is also defined in the following claims.

What is claimed is:

1. A method for manufacturing an in-line connector comprising:
    encapsulating an in-line connector stack with an encapsulation layer to form an encapsulated in-line stack, wherein:
        the encapsulation layer comprises an elongated body defining a bore having a continuous length, a plurality of slots, and a section of the elongated body that is formed as a continuous integral element in a radial direction;
        the in-line connector stack comprises a plurality of seal elements, a plurality of conductive contact elements, and a plurality of canted coil springs in contact with the plurality of conductive contact elements;
    sliding the in-line connector stack inside the bore so that at least a portion of the in-line connector stack slides past the section that is continuous in the radial direction;
    wherein a non-conductive end cap comprising an opening is disposed at each end of the in line connector stack; and
    aligning the plurality of conductive contact elements with the plurality of slots on the encapsulation layer; and
    wherein each of the plurality of canted coil springs is located in a groove comprising a back wall and two side walls formed from a combination of a conductive material and a non-conductive material.

2. The method of claim 1, wherein the encapsulation layer seals a plurality of seams formed between adjacent pairs of seal elements and conductive contact elements.

3. The method of claim 1, wherein the snap fit end cap has an entry annular seal for sealing against a lead cable.

4. The method of claim 1, wherein the in-line connector stack is placed into the bore through one end of the encapsulation layer.

5. The method of claim 1, further comprising placing the encapsulated in-line stack into a bore of a pre-formed header.

6. The method of claim 5, wherein the encapsulated in-line stack is pre-tested prior to placing into the bore of the header.

7. The method of claim 5, further comprising engaging a snap fit end cap against an end opening of the header to retain the encapsulated in-line stack within the bore of the pre-formed header.

8. The method of claim 7, wherein the snap fit end cap and the bore of the header exert an axial compressive force on the encapsulated in-line stack.

9. The method of claim 5, wherein the pre-formed header comprises a plurality of slots.

10. The method of claim 9, wherein the plurality of slots of the pre-formed header are aligned with the plurality of slots on the encapsulation layer.

11. The method of claim 1, wherein the encapsulation layer comprises a non-conductive continuous cylindrical body forming a cavity for receiving the plurality of seal elements and conductive contact elements.

12. A connector header assembly comprising a header comprising a bore, an in-line connector stack comprising a plurality of alternating seal elements, a plurality of canted coil springs, and conductive contact elements encapsulated by an encapsulation layer to form an encapsulated in-line stack positioned inside the bore of the header, and a snap fit end cap comprising a bore mechanically engaged to the header to retain the encapsulated in-line stack within the bore of the header, the snap fit end cap and the header define a seam therebetween, and wherein the header comprises a plurality of slots aligned with a plurality of slots formed on the encapsulation layer and wherein the encapsulation layer comprises an elongated body that is continuous along a length and continuous in a radial direction without a seam.

13. The connector header assembly of claim 12, further comprising a first end cap attached to a first end of the encapsulation layer and a second end cap attached to a second end of the encapsulation layer, said first and second end caps each comprising an opening.

14. The connector header assembly of claim 12, wherein the encapsulated in-line stack is formed before being placed inside the bore of the header.

15. The connector header assembly of claim 14, wherein the snap fit end cap and the bore of the header exert an axial compressive force on the encapsulated in-line stack.

16. The connector header assembly of claim 12, wherein the snap fit end cap comprises an opening for accessing a fastener.

17. The connector header assembly of claim 12, wherein the encapsulation layer seals a plurality of seams formed between adjacent pairs of seal elements and conductive contact elements.

18. The connector header assembly of claim 12, further comprising a second bore for receiving a second encapsulated in-line stack.

19. The connector header assembly of claim 12, further comprising an opening on the header for placing a holding ring therethrough.

20. A method for manufacturing an in-line connector comprising:
    forming an encapsulated in-line stack by sliding a plurality of seal elements, springs, and conductive contact elements through a firstend opening of a cylindrical housing comprising a bore, a continuous housing section along a radial direction, and the first end opening and a second end opening, said cylindrical housing further comprising a plurality of slots formed laterally of the first opening;
    engaging an end cap to the first end opening of the cylindrical housing;
    aligning the plurality of conductive contact elements with the plurality of slots on the cylindrical housing; and
    testing the encapsulated stack by applying an electrical signal across at least one of the conductive contact elements.

21. The method of claim 20, further comprising placing the encapsulated stack into a bore of a pre-formed header.

* * * * *